(12) United States Patent
Wang et al.

(10) Patent No.: US 8,155,727 B2
(45) Date of Patent: Apr. 10, 2012

(54) WRIST COIL FOR MAGNETIC RESONANCE IMAGING

(75) Inventors: Hai Ning Wang, ShenZhen (CN); Yan Hong Chen, ShenZhen (CN); Jian Min Wang, ShenZhen (CN)

(73) Assignee: Siemens Aktiengesellschaft, Munich (DE)

( * ) Notice: Subject to any disclaimer, the term of this patent is extended or adjusted under 35 U.S.C. 154(b) by 372 days.

(21) Appl. No.: 12/393,454

(22) Filed: Feb. 26, 2009

(65) Prior Publication Data

US 2009/0221906 A1 Sep. 3, 2009

(30) Foreign Application Priority Data

Feb. 29, 2008 (CN) .................. 2008 2 0003842 U

(51) Int. Cl.
*A61B 5/055* (2006.01)
(52) U.S. Cl. .................. 600/422; 324/318; 324/322
(58) Field of Classification Search .................. 600/422, 600/410, 411, 421; 324/318, 322
See application file for complete search history.

(56) References Cited

U.S. PATENT DOCUMENTS

| 5,543,710 | A | * | 8/1996 | Jones | 324/318 |
| 7,253,622 | B2 | * | 8/2007 | Saylor et al. | 324/318 |
| 7,394,256 | B2 | * | 7/2008 | Schubert et al. | 324/321 |
| 2006/0173284 | A1 | * | 8/2006 | Ackerman et al. | 600/422 |

* cited by examiner

*Primary Examiner* — Ruth S Smith
(74) *Attorney, Agent, or Firm* — Schiff Hardin LLP

(57) ABSTRACT

A wrist coil for magnetic resonance imaging has a tubular coil formed by a number of coil splicing units spliced together in succession, and an annular coil unit that is wound around the surface of the tubular coil. Since the annular coil unit is wound around the surface of the tubular coil, and the current direction in the annular coil unit is perpendicular to the current direction in each of the coil splicing units, when some of the coil splicing units in the tubular coil do not acquire signals due to the fact that their magnetic field direction is parallel to that of the main magnetic field direction, the annular coil unit will carry out signal acquisition. Furthermore, since the magnetic flux of the annular coil unit is relatively large, this ensures a relatively high signal-to-noise ratio in the acquired signals no matter whatever layout position is adopted for the wrist coil, thus reducing equipment costs and eliminating restrictions for clinical applications in the prior art.

3 Claims, 3 Drawing Sheets

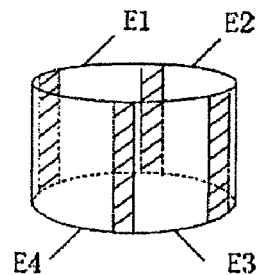
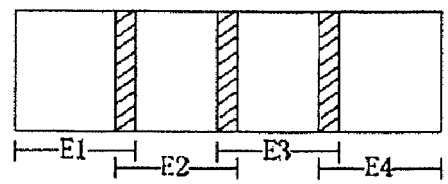
Fig. 1a (PRIOR ART)
Fig. 1b (PRIOR ART)
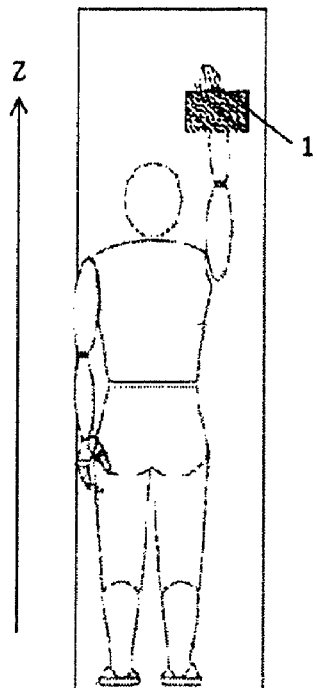
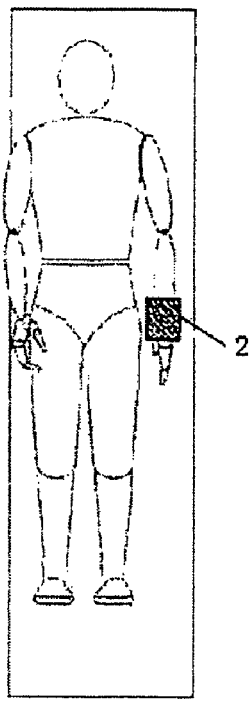
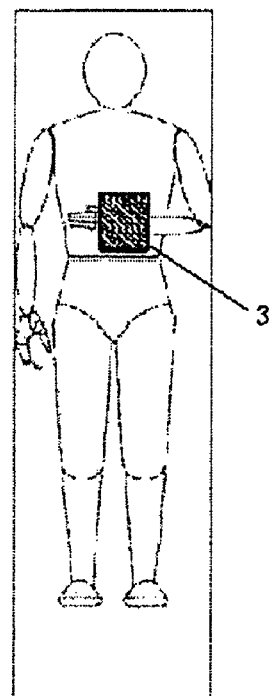
Fig. 2a (PRIOR ART)
Fig. 2b (PRIOR ART)
Fig. 2c (PRIOR ART)

WRIST COIL FOR MAGNETIC RESONANCE IMAGING

BACKGROUND OF THE INVENTION

1. Field of the Invention

The present invention relates to magnetic resonance imaging (MRI) technology and, particularly, to a wrist coil.

2. Description of the Prior Art

The basic working principles of MRI are that the hydrogen atoms (also other atoms, but the hydrogen atoms are the most commonly used) in human tissues will be directionally aligned under the effects of a fixed magnetic field. When applying radio-frequency pulses from outside, these hydrogen atoms will be displaced due to the effects of the radio-frequency pulses. After the radio-frequency pulses have ceased, these hydrogen atoms will be restored to their original states, and during the restoring process, signals generated by these hydrogen atoms are acquired and then the acquired signals are used in image reconstruction algorithm so as to obtain the image of human tissues.

Radio-frequency receiving coils (hereinafter referred to as coils) are devices used in MRI equipment for acquiring the signals. The coils can be classified according to their relationships with a human body as: head coils, body coils and surface coils; and they can be classified according to their shapes as: tubular coils, planar coils, helmet coils and segment coils, etc. A wrist coil is a tubular surface coil for carrying out scanning to a wrist part.

FIGS. 1(a) to 1(b) show the basic structure of a conventional coil. In FIG. 1(a) shows the shape of the wrist coil which is tubular and FIG. 1(b) is an exploded structural view of the existing wrist coil. The component units of the coil are coil units. In FIGS. 1(a) and 1(b), the illustration is made with the number of the coil units being four, and the coil units are indicated as E1 to E4.

It can be seen from the exploded structural view of the existing coil unit shown in FIG. 1(b) that the connection relationship between these coil units in the wrist coil is as follows. Starting from the first coil unit E1, the coil units in adjacent positions are spliced together in succession, then the first coil unit E1 and the last coil unit E4 are spliced with each other, in this way, a tubular coil formed by several coil units spliced together in succession is obtained, and the shape of the tubular coil is as shown in FIG. 1(a). In order to achieve a relatively good image quality, when constructing the tubular coil, the spliced parts between two adjacent coil units often have a certain overlap so as to form a spliced part, as shown in the shaded portions between every two adjacent coil units in FIGS. 1(a) and (b). In the following description, the coil units used to splice together and form a tubular coil are referred to as coil splicing units.

Currently in clinical applications, the wrist coils mainly have three layout positions as shown in FIGS. 2(a), (b) and (c).

FIG. 2(a) shows a first layout position wherein a patient lies facing down on a patient bed, with one arm stretched out in the head direction. A wrist coil 1 is placed around the patient's wrist, and the arm is the axis of the wrist coil 1.

FIG. 2(b) shows a second layout position wherein a patient lies facing up on a patient bed, with his other arms at the two sides of his body, a wrist coil 2 is placed around the patient's wrist, and the arm is the axis of the wrist coil 2.

FIG. 2(c) shows a third layout position wherein a patient lies facing up on a patient bed with one elbow bent and the arm on his stomach. The wrist coil 3 is placed around the patient's wrist, and the arm is the axis of the wrist coil 3.

Since existing coils are usually each designed for a particular layout position, if such a coil is applied to other positions, the signal-to-noise ratio of acquired signals will drop significantly. Below, with reference to the accompanying drawings, analysis is made of the wrist coil shown in FIGS. 1(a) and (b) it is laid out according to the three positions shown in FIGS. 2(a) 2(b) and 2(c), regarding the direction of the magnetic field direction of these coil splicing units and the signal-to-noise ratio levels of the acquired signals.

During the operating process of MRI equipment, each coil unit acquires corresponding signals, the acquired signals are vectors, which are referred to as radio-frequency output signals, and image reconstruction can be performed according to these radio-frequency output signals so as to obtain an image. When the direction of the magnetic field of a coil unit is perpendicular to the direction of the main magnetic field of the MRI equipment, the intensity of the signals acquired by the coil unit is the maximum; and when the direction of the magnetic field of the coil unit is parallel to the direction of main magnetic field of the MRI equipment, the coil unit does not acquire any signal.

According to the "right hand rule," the direction of main magnetic field of the MRI equipment will be along the positive direction or negative direction of the Z-axis shown in FIGS. 2(a) 2(b) and 2(c).

When the wrist coil shown in FIGS. 1(a) and 1(b) is laid out according to the first or the second layout position shown in FIGS. 2(a) 2(b) and 2(c), the arm is parallel to the Z-axis, namely, the axis of the wrist coil is parallel to the direction of the main magnetic field, therefore, these two layout positions are actually the same. FIG. 3(a) shows a schematic view of the relationship between the current direction in the coil splicing units of the wrist coil and the direction of the main magnetic field of the MRI equipment when the wrist coil shown in FIGS. 1(a) and 1(b) is laid out according to the first and the second positions shown in FIGS. 2(a) 2(b) and 2(c). For the sake of simplicity in the description, FIGS. 3(a) and 3(b) do not show the overlapped parts between the adjacent coil splicing units as shown in FIG. 1. Referring to FIG. 3(a), there exist two possibilities for the current direction in the coil splicing units: either upward or downward along the axial direction of the wrist coil. Since the axis of the wrist coil is parallel to the direction of main magnetic field, no matter whether the current directions in the coil splicing units are upward or downward along the axial direction of the wrist coil, here, the current directions of the four coil splicing units are all parallel to the direction of main magnetic field, therefore, the magnetic field directions of these four coil splicing units are all located in the plane perpendicular to the direction of the main magnetic field. Therefore, the magnetic field directions of these four coil splicing units are perpendicular to the direction of the main magnetic field, so that these four coil splicing units will all output radio-frequency output signals, and at this time, the signal-to-noise ratios of the acquired signals are relatively high.

When the wrist coil shown in FIGS. 1(a) and 1(b) is laid out according to the third layout position shown in FIG. 2(c), the arm is perpendicular to the Z-axis, namely, the axis of the wrist coil is perpendicular to the direction of the main magnetic field. FIG. 3(b) shows a schematic view of the relationship between the current direction of the coil splicing units of the wrist coil and the direction of the main magnetic field of the MRI equipment when the wrist coil shown in FIG. 1 is laid out according to the third position shown in FIG. 2(c). Referring to FIG. 3(b), two of the four coil splicing units will be parallel to the Z-axial direction, and the other two coil splicing units will be perpendicular to the Z-axial direction, and there are two possibilities for the current directions of the coil splicing units: either to the left or the right direction along the axial direction of the wrist coil. No matter whether the current directions of coil splicing units are to the left or right along the axial direction of the wrist coil, here, the magnetic field direction of the two coil splicing units perpendicular to the Z-axial direction will be perpendicular to the direction of the main magnetic field, and these two coil splicing units will output radio-frequency output signals. For the two coil splicing units being parallel to the direction of Z-axis, since the direction of their current is perpendicular to the direction of the main magnetic field, the magnetic field direction of these two coil splicing units will be parallel to the direction of the main magnetic field, and these two coil splicing units will not acquire any signal, and then they will not output radio-frequency output signals, which will cause a severe drop in the signal-to-noise ratio of the acquired signals.

It can be seen that, the wrist coil shown in FIGS. 1(a) and 1(b) is only applicable to the first or the second layout position shown in FIG. 2(b), but not applicable to the third layout position shown in FIG. 2(c).

In clinical applications the wrist coils are required to provide three layout positions as shown in FIGS. 2(a) 2(b) and 2(c), but the existing wrist coils cannot be adopted in those three layout positions at the same time. Therefore, in the prior art two types of different wrist coils have to be designed with the layout positions of these wrist coils restricted so as to meet the clinical application requirements. This has brought about problems in the following two aspects. First, providing two types of wrist coils at the same time increases equipment costs. Second, if in the MRI equipment only one type of wrist coil is provided, then there is at least one layout position that the MRI equipment cannot provide, which will limit its clinical application. For example: assuming that some MRI equipment is equipped only with the wrist coil applicable to the third layout position shown in FIG. 2(c), if a patient is relatively obese, the third layout position cannot be realized, for this reason, this patient would not be able to have a scan at the wrist part in this MRI equipment, which limits its clinical application.

SUMMARY OF THE INVENTION

In view of the situation, an object of the present invention is to provide a wrist coil that is applicable to various existing layout positions, so as to reduce equipment costs and relieve the restrictions on clinical applications.

The above object is achieved in accordance with the invention by a wrist coil having a tubular coil formed by a number of coil splicing units spliced together in succession, and having an annular coil unit, with the annular coil unit wound around the surface of the tubular coil.

Preferably, the axis of the annular coil unit and the axis of the tubular coil are coincident.

Preferably, the wrist coil is formed by two tubular coils wound respectively with said annular coil unit, wherein said two tubular coils are overlapped and spliced, and their axes are coincident and parts of their surfaces are overlapped.

The spliced parts of the coil splicing units of the two tubular coils are not overlapped.

The wrist coil mentioned above can further have signal synthesis modules, which are connected with two of the coil splicing units oppositely positioned in the same tubular coil, for synthesizing the radio-frequency output signals from the two oppositely positioned coil splicing units.

The wrist coil described above can also have a further signal synthesis module, for performing second synthesis of the previously synthesized signals.

In the wrist coil according to the invention because the annular coil unit is wound around the surface of the tubular coil, and the current direction of the annular coil unit is perpendicular to the current direction of each of these coil splicing units, when some of the coil splicing units in the tubular coil do not acquire signals due to the magnetic field direction thereof being parallel to the main field direction, the annular coil unit will acquire signals. Furthermore, the magnetic flux of the annular coil unit is relatively large, which ensures that the signal-to-noise ratio of the acquired signals is always relatively high no matter what position the wrist coil of the present invention is placed in, thus reducing equipment costs and eliminating restrictions on clinical applications that exist in the prior art.

Furthermore, in the preferred embodiments of the present invention, a wrist coil is provided that has two tubular coils each wound with an annular coil unit, with the two tubular coils being overlapped and spliced with each other and their axes are coincident. In order to achieve a better image quality, the present invention uses a mode as initially described for splicing two adjacent coil units to overlap and splice together the two tubular coils. Namely, the surfaces of the two tubular coils are made to have a certain overlap. Furthermore, in order to reduce the level of coupling between the radio-frequency output signals of the coil splicing units as much as possible, when splicing together the two tubular coils, the present invention uses a mode in which these spliced parts of the coil splicing units of these two tubular coils are not overlapped. Namely, the two tubular coil units are made to offset by a certain distance.

In order to further improve image quality, the present invention also has a signal synthesis module for synthesizing the radio-frequency output signals of the coil splicing units. Preferably, the signal synthesis module can be connected to the two coil splicing units oppositely positioned in the same tubular coil, so as to synthesize the radio-frequency output signals of said two oppositely positioned coil splicing units. When the number of the receiving channels in MRI equipment is less than the number of the coil splicing units, some channels with relatively weak synthesized signals can be discarded to match the number of receiving channels.

DESCRIPTION OF THE DRAWINGS

FIGS. 1(a) to 1(b) show the basic structure of a conventional wrist coil.

FIGS. 2(a) to 2(c) show schematic diagrams of three layout positions of the conventional wrist coil.

DESCRIPTION OF THE PREFERRED EMBODIMENTS

The underlying concept of the present invention is that on a wrist coil having a tubular coil, at least one annular coil unit wound around the surface of the tubular coil, so as to utilize the characteristics that the current direction in the annular coil unit is perpendicular to the current direction of each of the coil splicing units, and that the magnetic flux of the annular coil unit is relatively high, so as to solve the problem that a conventional wrist coil is not applicable to all layout positions.

Figure 4:
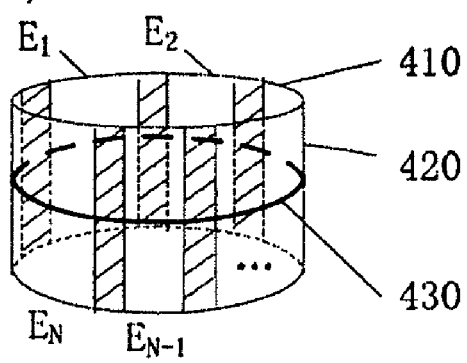
FIG. 4 shows the basic structure of the wrist coil of the present invention.

FIG. 4 is a structural diagram of the wrist coil of the present invention. Referring to FIG. 4, the wrist coil has the following components:

A tubular coil 420 is formed by a number of coil splicing units 410 spliced together in succession. In FIG. 4, $E_1$, $E_2$ ... $E_{N-1}$, $E_N$ represent the coil splicing units, and the shaded parts between every two adjacent coil splicing units 410 indicate that there exists a certain overlapping at the splicing part of the two coil splicing units, thereby forming the spliced parts.

The wrist coil also has an annular coil unit 430, and this annular coil unit 430 is wound around the surface of said tubular coil 420.

In this wrist coil, the axis of the annular coil unit 430 and the axis of the tubular coil are coincident.

Figure 5:
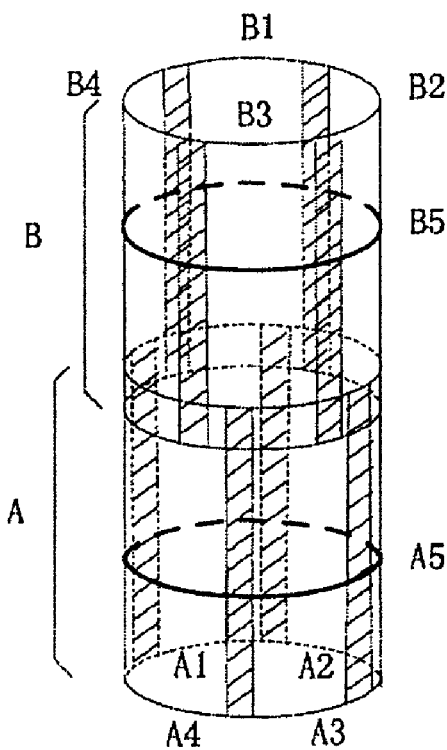
FIG. 5 shows the basic structure of a preferred embodiment of the wrist coil according to the present invention.

In order to achieve a relatively high signal-to-noise ratio and to control the equipment costs within a relatively low range, preferably, the wrist coil can have two tubular coils each wound with the annular coil unit 430. Taking the case that each tubular coil has four coil splicing units as an example, FIG. 5 shows a structural diagram of a preferred embodiment of a wrist coil of the present. Referring to FIG. 5, the wrist coil has eight coil splicing units and two annular coil units.

The coil splicing units A1 to A4 are spliced together in succession to form the tubular coil A, and an annular coil unit A5 is wound around the surface of the tubular coil A.

The coil splicing units B1 to B4 are spliced together in succession to form the tubular coil B, and an annular coil unit B5 is wound around the surface of the tubular coil B.

The tubular coil A and the tubular coil B are overlapped and spliced together with each other, and the axes of the two are coincident. Furthermore, the surfaces of the tubular coil A and the tubular coil B are partially overlapped, as shown in the part outlined with a dotted line between the tubular coil A and the tubular coil B in FIG. 5. Therefore, the height of the wrist coil obtained after overlapping and splicing together the tubular coil A and the tubular coil B is less than the sum of the heights of the tubular coil A and the tubular coil B.

In order to reduce as much as possible the level of coupling among the radio-frequency output signals of these coil splicing units, when splicing together the tubular coil A and the tubular coil B, the splicing parts of the coil splicing units of the two tubular coils are made not to overlap, namely, each splicing part of these two tubular coils is made to offset by a certain distance.

For example, referring to FIG. 5, there are four spliced parts in the tubular coil A, namely, the spliced part between A1 and A2, the spliced part between A2 and A3, the spliced part between A3 and A4, and the spliced part between A4 and A1.

As also shown in FIG. 5, there are four spliced parts in the tubular coil B, namely, the spliced part between B1 and B2, the spliced part between B2 and B3, the spliced part between B3 and B4, and the spliced part between B4 and B1.

The abovementioned "the splicing parts of the coil splicing units of the two tubular coils are made not to overlap" means that the four splicing parts in the tubular coil A and the four splicing parts in the tubular coil B are made not to overlap, instead they are offset by a certain distance.

Below, the conditions for signal acquisition, when the wrist coil of the present invention is applied to the various layout positions, are analyzed.

Figure 3A:
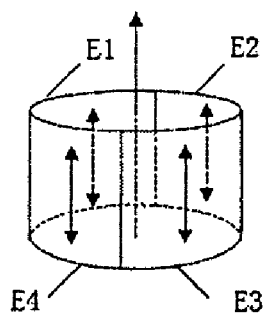
FIGS. 3(a) and 3(b) show schematic diagrams of the relationships between the current directions of these coil splicing units of the wrist coil and the direction of the main magnetic field of MRI equipment when the wrist coil shown in FIGS. 1(a) and 1(b) is laid out according to the three positions shown in FIGS. 2(a) 2(b) and 2(c).

(1) When applying the wrist coil of the present invention to the first and the second layout positions as shown in FIGS. 2(a) 2(b) and 2(c) it can be seen according to the description regarding FIG. 3(a) that the current directions of A1 to A4 and B1 to B4 are all parallel to the direction of the main magnetic field, the magnetic field directions of the eight coil splicing units A1 to A4 and B1 to B4 are all located in the plane perpendicular to the direction of the main magnetic field. Therefore, the magnetic field directions of the eight coil splicing units are perpendicular to the direction of the main magnetic field. Here, all of the eight coil splicing units will acquire signals, and they output RF output signals, and the signal-to-noise ratios of acquired signals are relatively high.

Moreover, A5 and B5 do not acquire signals because their magnetic field direction is parallel to the direction of the main magnetic field, and they do not output RF output signals.

It can be seen that, when applying the wrist coil of the present invention to the first and the second layout positions as shown in FIGS. 2(a) and 2(b), the level of signal-to-noise ratio of the acquired signals is equivalent to the situation of there being no annular coil unit added, while according to the background art section, the signal-to-noise ratio of acquired signals in this situation is high, and relatively good image quality can be obtained.

Figure 3B:
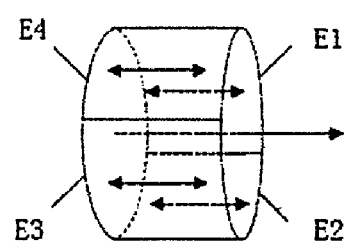

(2) When applying the wrist coil of the present invention to the third layout position as shown in FIG. 2(c), it can be seen according to the description about FIG. 3(b) that, two units of each tubular coil will be parallel to the Z-axis, the other two will be perpendicular to the Z-axis. Assuming A1, A3, B1 and B3 are parallel to the Z-axial direction, A2, A4, B2 and B4 are perpendicular to the Z-axial direction. At this time, the magnetic field directions of A2, A4, B2 and B4 are perpendicular to the direction of the main magnetic field, and all of them will output RF output signals, and the signal-to-noise ratio of the acquired signals will be relatively high, and A1, A3, B1 and B3 will not acquire signals and not output radio-frequency output signals due to their magnetic field directions being parallel to the main field direction. Moreover, the magnetic field directions of A5 and B5 will be perpendicular to the main field direction, and they both will output radio-frequency output signals, and since A5 and B5 have a relatively large magnetic flux, the signal-to-noise ratio of the signals acquired by them will also be relatively high, so as to compensate the signals that A1, A3, B1 and B3 fail to acquire, making the signal-to-noise ratio of the totality of acquired signals a high level.

It can be seen from the above description that, no matter which layout position to which the wrist coil according to the present invention is applied, a high signal-to-noise ratio will be achieved, thereby relieving the restriction of the prior art to the layout positions of the wrist coil. Moreover, the wrist coil of the present invention only adds the annular coil units on the basis of the existing wrist coil, which in comparison with the fact that in the prior art it needs to provide various wrist coils applicable to different layout positions, the costs are obviously much lower.

It is well known that the radio-frequency output signals acquired by these coil units in the coil need to be sent to the image reconstruction system in the MRI equipment, then the image reconstruction system performs image reconstruction on the basis of the received signals. When the number of receiving channels in the image reconstruction system is less than the number of coil units in the coil, the radio-frequency output signals outputted by the coil units need to be synthesized to match the required number of the receiving channels. Even when the number of receiving channels is not less than the number of coil units, in order to obtain a more uniform image, a certain strategy can also be used to perform synthesis to these channels of radio-frequency output signals. For this purpose, the wrist coil according to the invention also has a signal synthesis module in the wrist coil to perform synthesis to signals. Preferably, the signal synthesis module can be connected with two coil splicing units opposite positioned in the same tubular coil, so as to carry out synthesis to the radio-frequency output signals of two coil splicing units opposite positioned to obtain a better image quality. In conjunction with the wrist coil shown in FIG. 5, A1 and A3 are two coil splicing units oppositely positioned in said same tubular coil of the present invention. Similarly, A2 and A4, B1 and B3, B2 and B4 are also the two coil splicing units oppositely positioned in said same tubular coil of the present invention.

Figure 6:
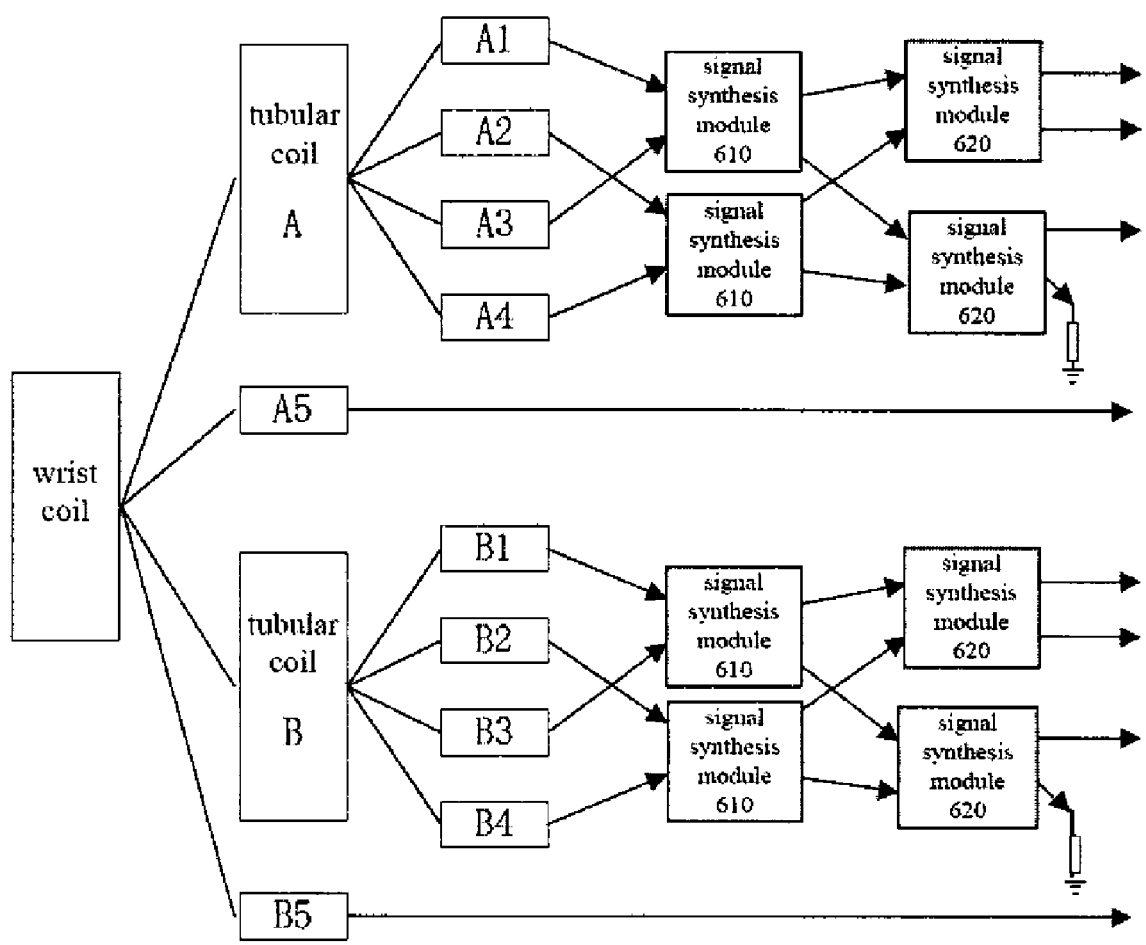
FIG. 6 is a schematic diagram of the operating principles for performing signal synthesis of the radio-frequency output signals acquired by the wrist coil shown in FIG. 5.

FIG. 6 is a schematic diagram of the operating principles for performing signal synthesis to the radio-frequency output signals acquired by the wrist coil of the present invention shown in FIG. 5. Referring to FIG. 6, the processing flow of the signal synthesis includes the processing of the radio-frequency output signals of the annular coil units and the processing of the radio-frequency output signals of coil splicing units in the tubular coil.

As to the annular units, their radio-frequency output signals are outputted directly, namely, as shown in FIG. 6, the radio-frequency output signals of A5 and B5 are outputted directly.

As to the coil splicing units in the tubular coil, it is necessary to perform synthesis twice, as follows.

First, the signal synthesis module 610 carries out synthesis for the first time to the radio-frequency output signals from the two coil splicing units oppositely positioned in the same tubular coil, so as to obtain eight channels of signals. Namely, as shown in FIG. 6, the radio-frequency output signals of A1 and A3 are sent to the signal synthesis module 610 for carrying out synthesis, so as to obtain two channels of signals. The radio-frequency output signals of A2 and A4 are sent to the signal synthesis module 610 for carrying out synthesis to obtain two channels of signals. The radio-frequency output signals of B1 and B3 are sent to the signal synthesis module 610 for carrying out synthesis to obtain two channels of signals. The radio-frequency output signals of B2 and B4 are sent to the signal synthesis module 610 for carrying out synthesis to obtain two channels of signals. Thus eight channels of signals are obtained.

Then, the signal synthesis module 620 carries out second synthesis to the eight channels of synthesized signals to obtain eight channels of signals. Namely, as shown in FIG. 6, the first channel of signals synthesized from A1 and A3 and the first channel of signals synthesized from A2 and A4 are sent to the signal synthesis module 620 for carrying out synthesis to obtain two channels of signals, and in a similar way to produce the rest, so that eight channels of signals after the second synthesis will be obtained.

If the number of receiving channels is eight, two of the eight channels of signals obtained after the second synthesis can be discarded. For example: one channel of weaker signals in the tubular coil A and one channel of weaker signals in the tubular coil B is discarded.

It can be seen from the above description that, in the wrist coil according to the present invention, since the annular coil unit is wound around the surface of the tubular coil and the current direction in the annular coil unit is perpendicular to the current directions of all coil splicing units in the tubular coil, when some coil splicing units of the tubular coil do not acquire signals due to the fact that their magnetic field direction is parallel to the main field direction, the annular coil unit will perform signal acquisition. Furthermore, the magnetic flux of the annular coil unit is relatively high, so that no matter in which position the wrist coil of the present invention is laid out, the signal-to-noise ratios of acquired signals are always sure to be relatively high, thus reducing the equipment costs and eliminating restrictions on clinical applications in the prior art.

Furthermore, in preferred embodiments of the present invention, a wrist coil has two tubular coils each wound with an annular coil unit. The two tubular coils are overlapped and spliced together with each other and their axes are coincident. In order to achieve a better image quality, the present invention splices together the two adjacent coil splicing units in the manner initially described, namely, making the surface of the two tubular coils have a certain overlap. In addition, in order to reduce as much as possible the level coupling between the radio-frequency output signals of the coil splicing units, the present invention causes the spliced parts of the coil splicing units of these two tubular coils not to overlap during the overlapping and splicing together of the two tubular coils, by the spliced parts of two tubular coils being offset by a certain distance.

In order to further improve the image quality, the present invention also includes a signal synthesis module to perform synthesis to the radio-frequency output signals of the coil splicing units. Preferably, the signal synthesis module can be connected to the two coil splicing units opposite positioned in the same tubular coil, so as to perform synthesis to the radio-frequency output signals of these two opposite positioned coil splicing units. When the number of receiving channels in the MRI equipment is less than the number of the coil splicing units, some channels of relatively weak signals obtained by synthesizing can also be discarded, so as to match the number of receiving channels.

Although modifications and changes may be suggested by those skilled in the art, it is the intention of the inventors to embody within the patent warranted hereon all changes and modifications as reasonably and properly come within the scope of their contribution to the art.

We claim as our invention:

1. A wrist coil for magnetic resonance imaging, comprising;
   a first tubular coil having a first tubular coil surface with a shape and dimensions configured to fit extracorporeally around a human wrist;
   said first tubular coil being formed by a plurality of first coil splicing units that are spliced together in succession at spliced parts of said first coil splicing units;
   a first annular coil unit wound around said first tubular coil surface;
   a second tubular coil having a second tubular coil surface also with a shape and dimensions configured to fit extracorporeally around a human wrist;
   said second tubular coil being formed by a plurality of second coil splicing units that are spliced together in succession at spliced parts of said second coil splicing units;
   a second annular coil unit wound around said second tubular coil surface;
   said first and second tubular coils being spliced together by overlapping each other at the respective first and second tubular coil surfaces thereof, with the respective sliced parts of the first and second coil splicing units being offset from each other and not overlapping each other; and said first tubular coil having a first tubular coil axis and said second tubular coil having a second tubular coil axis, said first and second tubular coil axes being coincident when said first and second tubular coils are spliced together.

2. A wrist coil as claimed in claim 1 comprising a plurality of signal synthesis modules each connected to one pair of said coil splicing units, among a plurality of different pairs of said coil splicing units that are oppositely positioned in at least one of said first and second tubular coils, each signal synthesis module being configured to synthesize radio-frequency output signals respectively emitted from said one pair of said coil splicing units connected thereto.

3. A wrist coil as claimed in claim 2 wherein each of said signal synthesis modules has an output, and comprising a further signal synthesis module connected to said outputs of said signal synthesis modules, configured to perform a second synthesis of said radio-frequency output signals.

* * * * *